United States Patent [19]

Ryder

[11] Patent Number: 5,533,497
[45] Date of Patent: Jul. 9, 1996

[54] SIDESTREAM AEROSOL GENERATOR AND METHOD IN VARIABLE POSITIONS

[76] Inventor: Steven L. Ryder, 1334 W. Woodcrest Ave., Fullerton, Calif. 92633

[21] Appl. No.: 410,876

[22] Filed: Mar. 27, 1995

[51] Int. Cl.$^6$ ................................................ A61M 11/00
[52] U.S. Cl. ........................... 128/200.21; 128/200.12; 261/78.2; 239/338
[58] Field of Search ..................... 128/200.14, 200.18, 128/200.21, 200.12, 200.13, 204.14; 261/78.2, DIG. 65; 239/392, 338, 346

[56] References Cited

U.S. PATENT DOCUMENTS

| | | | |
|---|---|---|---|
| 4,512,341 | 4/1985 | Lester | 128/200.21 |
| 4,566,452 | 1/1986 | Farr | 128/200.21 |
| 4,657,007 | 4/1987 | Carlin et al. | 128/200.18 |
| 4,746,067 | 5/1988 | Svoboda | 239/338 |
| 4,792,097 | 12/1988 | Kremer, Jr. et al. | 239/338 |
| 5,008,048 | 4/1991 | Ryder | 261/78.2 |
| 5,239,969 | 8/1993 | Bellm | 128/200.18 |
| 5,379,760 | 1/1995 | Ryder | 128/200.21 |

*Primary Examiner*—Edgar S. Burr
*Assistant Examiner*—Eric P. Raciti

[57] ABSTRACT

A device and method for the aerosolization of a liquid, includes a liquid reservoir having a three dimensional geometric shape within a hollow cylindrical housing and a gas nozzle in the liquid reservoir. An internal component having a three dimensional geometric shape conforming to the internal walls of the liquid reservoir, having a liquid conduit and a liquid orifice, and minimally spaced from the internal walls of the liquid reservoir and the gas nozzle. The gas nozzle coupled to pressurized gas source, produces a high velocity gas stream which exits through the liquid orifice. A subatmospheric pressure is created within the minimal space between the liquid conduit, and gas nozzle. The liquid is aspirated from the minimal space between the internal component and the internal walls of the liquid reservoir, to the minimal space between the liquid conduit, and gas nozzle and out the liquid orifice. A removable threaded cap with an aerosol outlet on the cylindrical housing, provides a seal between the inner surface of the cap, and the region of the minimal space between the internal component, and the internal walls of the liquid reservoir. The seal reduces the quantity of air aspirated from the minimal space, with improved aerosol output. As a result of the geometrical shape of the internal component conforming to the internal geometrical shape of the liquid reservoir, the device will generate an aerosol in any orientation from the vertical to above the horizontal positions.

15 Claims, 3 Drawing Sheets

SIDESTREAM AEROSOL GENERATOR AND METHOD IN VARIABLE POSITIONS

FIELD OF THE INVENTION

This invention relates generally to pneumatically operated aerosol generators or nebulizer's for the aerosolization of a liquid medication utilized in medicine for the treatment of pulmonary disease.

BACKGROUND OF THE INVENTION

In the medical field, the classification of the nebulizer is either mainstream or sidestream. The difference is due to the production of aerosol from the device relative to the main gas flow. For example, by definition with a mainstream nebulizer, main gas flow passes directly through the device and will admix with the carrier gas and aerosol particles. In comparison with a sidestream nebulizer, aerosol with the carrier gas simply drifts out of the device via a conduit and is added to the the main gas flow.

The most predominately prescribed nebulizer is the sidestream due to its simplicity for patient use and low cost.

Presently, in the field of respiratory care several popular versions of the sidestream small volume nebulizer are employed to administer an aerosol of liquid medication.

An example of the basic sidestream nebulizer is U.S. Pat. No. 4,566,452 sets forth a NEBULIZER issued to Farr, a nebulizer having a housing defining a liquid reservoir, a gas nozzle with inlet for introduction of gas to the nozzle. A liquid inlet which is spaced from the gas nozzle for introducing liquid to the gas nozzle as gas flows through the gas orifice. A liquid passage extends along and spaced from a portion of a sidewall which defines the liquid reservoir.

The major disadvantage of the Farr nebulizer is that the device must be held nearly at a vertical position which is necessary to aspirate and aerosolize the bulk of the liquid, and the device will only aspirate the liquid in one particular plane in the horizontal orientation.

Notably, in the United States, a very frequently prescribe small volume sidestream nebulizer is U.S. Pat. No. 4,512,341 issued to Lester which sets forth a NEBULIZER WITH CAPILLARY FEED, the feed to the spray nozzle is through a narrow space between the flat bottom of the liquid reservoir and a flange fixed to the bottom of the spray nozzle, liquid is drawn toward the nozzle by capillary action and aspiration at any orientation of the nebulizer between vertical and horizontal.

Of particular interest, are nebulizer's that will provide an aerosol at different positions or orientation of the device, particularly between the vertical and the horizontal This is necessary to better accommodate the position of the patient, or if the nebulizer is not held substantially vertical, the nebulizer will continue to produce an aerosol and reduce the wastage of medication.

The Lester Patent sets forth a nebulizer to provide aspiration of liquid at any orientation between the vertical an the horizontal. It has been observed that the device will not aspirate the liquid medication continuously in the horizontal orientation, when the volume of liquid has reached critical level for aspiration. The current method employed for the manufacture of plastic components on a large scale, is injection molding. For uniform wall thickness, both the reservoir and cap must have positive parallel draft angles required by the injection molding process to inexpensively manufacture the Lester sidestream nebulizer. The draft angles are typically from 1 to 3 degrees, which are the recommended standards in the industry. The draft angles of the nebulizer with the instilled initial volumes do not dramatically effect the performance of aerosol output when the nebulizer is in the horizontal position. In contrast, draft angles do effect the efficiency of aspiration and is substantially reduced with decreased, small volumes since the liquid is directed away from the described flange. This can result in aspiration stopping altogether, and therefore no production of aerosol. More will be explained later in detail when comparing the prior art nebulizer to the present invention.

Another example of a sidestream nebulizer, is U.S. Pat. No. 4,746,067 issued to Svoboda sets forth a LIQUID ATOMIZING DEVICE AND METHOD, the device may be operated in either a a horizontal position or vertical position by providing a liquid passage to the perimeter of the liquid reservoir by means of an angled liquid conduit formed between a pair of cone members. The Svoboda sidestream nebulizer attempts to correct for the draft angle to maintain the level of liquid in the horizontal position toward an annular opening for aspiration of the liquid. Nevertheless, to construct the liquid container by injection molding methods with the draft angle that will cause the liquid to be directed toward the annular opening, the liquid container is constructed of two parts, an outer cylindrical tapered wall, and a bottom wall consisting of a cone which is attached to the liquid container. Since the nebulizer shown has no removable threaded cap, the nebulizer cannot be disassembled for cleaning and possible reuse. Therefore, the sidestream nebulizer as illustrated is impractical. Also the additional manufacturing costs associated with the assembly of the liquid container. It has been observed, that the Svoboda sidestream nebulizer currently utilized in the medical field has a liquid container constructed of having positive draft angles and a removable threaded cap for disassembly, and thus not having the negative draft angles as depicted. When the Svoboda sidestream nebulizer is in the horizontal position, because of the positive draft angles, the same inherent problem exists as with the Lester sidestream nebulizer.

U.S. Pat. No. 5,008,048 issued to Ryder sets forth a POSITION INSENSITIVE ASPIRATOR, a device for aspirating liquids which is operable from any position or orientation. Includes a hollow housing communicating with a source of carrier gas and a a source of gas under pressure. A nozzle is disposed within the hollow housing through which the pressurized gas is directed to produce a high speed stream of gas. An entrainment member defining an aspiration chamber for liquid is disposed in the housing with the aspiration chamber immediately adjacent to the nozzle outlet in the housing. A multidirectional liquid flow path is defined by the entrainment member edge portions to provide fluid communication regardless of orientation of the device. Albeit this apparatus will achieve the generation of an aerosol regardless of position, it requires more than a few parts, and is preferentially designed for a mainstream configuration which is specifically used in connection with mechanical ventilators.

When considering the dispensing of pulmonary aerosol treatments via a sidestream nebulizer, in most cases it is not essential that a nebulizer function in every orientation.

At present, the prior art sidestream nebulizer will only operate between the vertical and horizontal, however the major benefit of the present invention will aspirate and therefore aerosolize the liquid medication from the vertical to above the horizontal. This will greatly facilitate aerosol therapy for the patient.

Although the forgoing described devices are representative of the prior art, there remains nonetheless a continuing need to improve the performance and capability of aerosol generators, specifically small volume sidestream nebulizers.

It is the object of this invention to provide a small volume sidestream aerosol generator which will be fully functional in the vertical to above the horizontal orientation.

Another object of the invention is to efficiently aspirate the liquid medication to generate an aerosol, at the different positions as described above.

It is the object of the invention to provide the therapeutic range of aerosol particle size from the vertical to above the horizontal.

A further object of the invention is to provide a facile approach concerning the construction and manufacturing of the device. Maintaining or minimizing cost for a sidestream nebulizing apparatus which will generate an aerosol in variable positions

SUMMARY OF THE INVENTION

In accordance with the present invention, the device relates to a new and improved sidestream aspirator or nebulizer. The purpose is to provide an aerosol delivery of liquid medication to the lungs of the patient primarily during acute and routine therapy. The present invention will provide a greater range for the administration of an aerosol, particularly from the vertical to above the horizontal. Therefore more efficient aspiration of the liquid medication when compared to existing prior art sidestream nebulizer's.

In general, the preferred embodiment is comprised of three parts. First a housing, the geometrical configuration of the invention is designed to comply with well established injection molding, manufacturing methods. Heretofore, a significant distinguishable feature of the invention compared to existing prior art sidestream nebulizer's, is the one piece construction with the required draft angles that will sustain aspiration of liquid from the vertical to above the horizontal. Therefore the angled aspects of the internal dimensions, allow liquid to gravitate to the regions within the housing of the nebulizer for efficient aspiration, ranging from the vertical to above the horizontal. A gas nozzle is disposed in the housing.

A second component integrated with a liquid conduit, is an internal component, which is juxtaposed within and is minimally spaced from the internal walls of the liquid reservoir, to provide a liquid pathway to the gas nozzle.

The internal component may, by way of example, be configured as a U-shape, a V-shape or a square-cornered U-shape, having the same above-described function.

A third part is the threaded cap. The multipurpose threaded cap serves to contain the liquid medication, to convey the aerosol via a cylindrical conduit, positioned through and superior to the cap. Below this conduit is a baffle and diffuser to finely divide the aerosol particles, which drift into the main gas flow via the aerosol exit windows. Furthermore, essential to the invention, which will be described in detail, the function of the cap will not only provide a seal for the housing but also provide a seal interposed above the internal wall of the housing and the internal component.

BRIEF DESCRIPTION OF THE DRAWINGS

The features of the present invention, which are believed to be novel, are set forth with particularity in the appended claims. The invention, together with the further objects and advantages thereof, may be best understood by reference to the following description taken in conjunction with the accompanying drawings, in the several figures of which like reference numerals identify like elements and in which:

DESCRIPTION OF THE PREFERRED EMBODIMENT OF THE INVENTION

Figure 1:
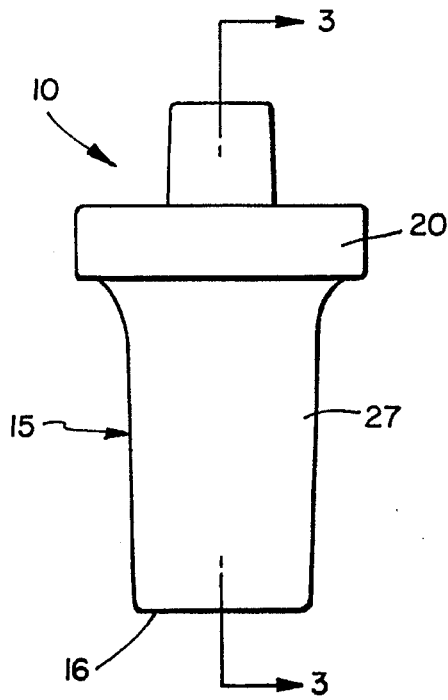
FIG. 1 sets forth a front view of the nebulizer constructed in accordance with the present invention.
Figure 2:
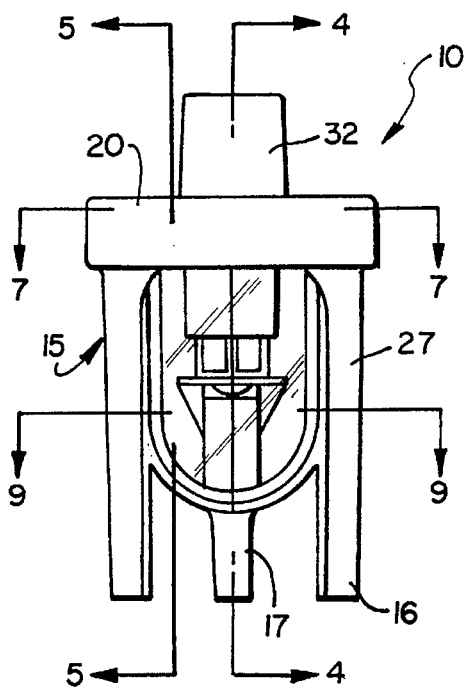
FIG. 2 sets forth a side view of the nebulizer constructed in accordance with the present invention.

In accordance with the present invention, FIG. 1 and FIG. 2 sets forth a front and side elevation view respectively of a small volume aerosol generator or nebulizer and generally referenced by numeral 10. Nebulizer 10 includes a cap 20 and a housing 15. The nebulizer housing 15 can be constructed of any suitable material including thermoplastics such as K-Resin® and cap 20 such as polypropylene.

Figure 3:
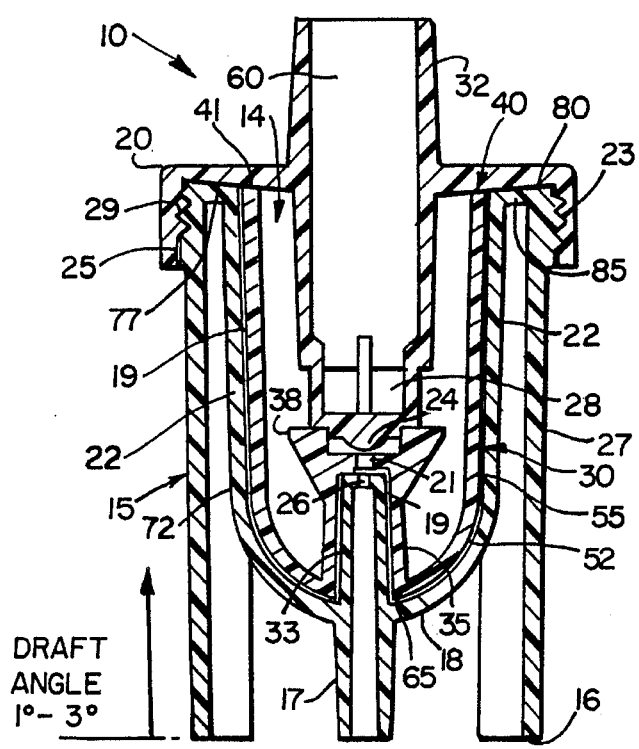
FIG. 3 sets forth a section view of the present invention taken along section lines 3—3 in FIG. 3.
Figure 4:
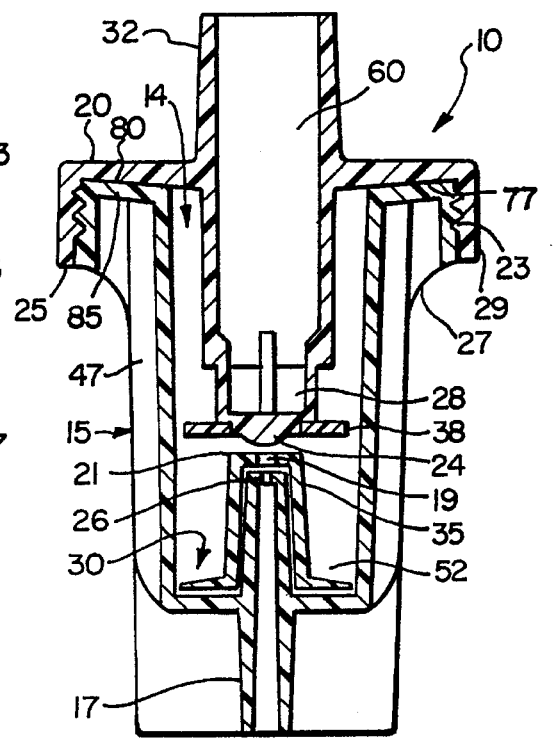
FIG. 4 sets forth a section view of the present invention taken along section lines 4—4 in FIG. 2.

Referring to FIG. 3, and FIG. 4, housing 15 is virtually comprised of two main parts. A liquid reservoir which is comprised of a first bottom section which is convexly curved upward having an inverted arc of somewhat less than 180 degrees with a width to form a semicircular strip or band 18. Extending from the convexly curved, semicircular band 18, having the same width, and to a slight degree, are two divergent planar walls 22 to form the upper section. To complete the enclosure of the liquid reservoir, and having a corresponding divergence, perpendicular and connected to the two divergent planar walls between both sides to the bottom of the semicircular band 18 are two adjacent divergent walls 47. The liquid reservoir 14 thus described, is essentially constructed within a second part a cylindrical shell 27. The two divergent planar walls 22 are connected and supported by the wall of cylindrical shell 27. The upper end wall 85 which is a perpendicular continuation of the cylindrical shell 27, is conically angled downward and also contains and supports the liquid reservoir 14 at its top surface. An external annular surface 25 at the upper end of the cylindrical shell 27, will provide a foundation for an external thread 23, to accommodate a removable cap 20 having an internal thread 29. The lower end of the cylindrical shell 27 will provide a base 16 to stand and stabilize and to conveniently fill the nebulizer 10 with liquid medication. Bilateral windows are constructed by sectioning through each side of the cylindrical shell 27, 180 degrees with respect to each section. The windows expose the two adjacent walls 47 for improved visualization of the liquid level of the nebulizer 10. Although for descriptive purposes, housing 15 was detailed as two parts, it is in general a single component, and it can be injection molded into one element.

Figure 7:
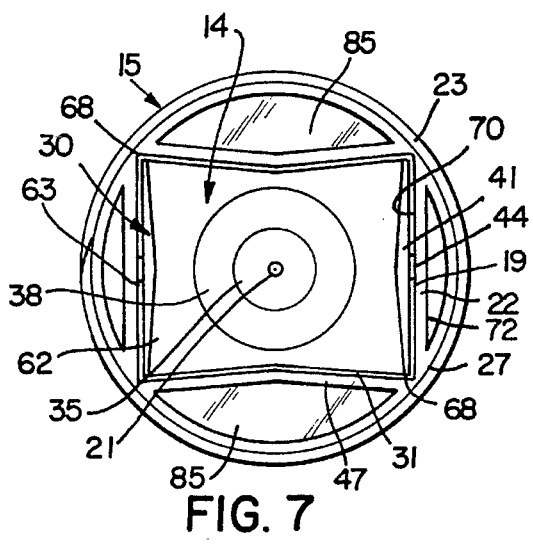
FIG. 7 sets forth a top view of the housing of the present invention taken along section lines 7—7 in FIG. 2.

Referring to FIG. 7 showing the top view of housing 15, the adjacent divergent walls 47 of the liquid reservoir 14 are inwardly angled. If in the event the nebulizer 10 is oriented in the horizontal orientation with either adjacent wall 47 facing downward, the liquid will gravitate to the corner regions at the junction of adjacent divergent walls 47 and divergent planar walls 22.

Figure 6:
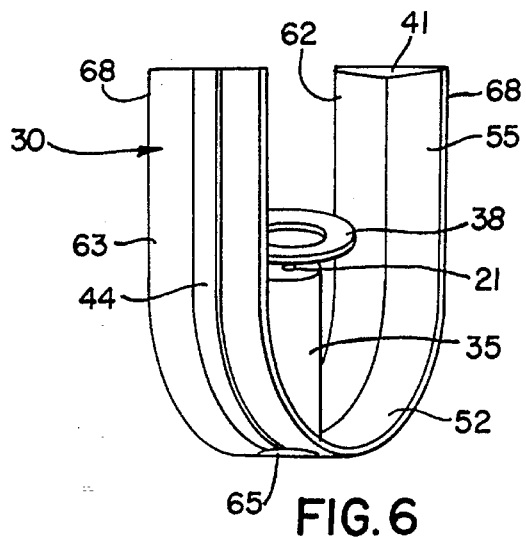
FIG. 6 sets forth a perspective view of the internal component of the present invention.

Returning to FIG. 3, an internal component 30 comprising first, a bottom section which is convexly curved upward having an inverted arc of slightly less 180 degrees, with a width to form a semicircular strip or band 52. Extending from the convexly curved, semicircular strip region having the same width are two diverging planar projections 55. From a side view which is perpendicular to the described geometrical configuration, beginning with the bottom convexly curved, semicircular strip 52, to the length of the two diverging planar projections 55, there is a corresponding angle of divergence. This conforms with the internal geometry juxtaposed within the liquid reservoir 14. The described internal component 30 is depicted in the perspective view of FIG. 6. In the lower region halfway and projecting upward out of the semicircular band 52, a liquid conduit 35, which supports a baffle 38 in the configuration of a washer. When the cap 20 is threaded to the housing 15, the dimension of the outer diameter of the diffuser 24 and the internal diameter of the baffle 38 is provided with a close enough tolerance to permit free rotation and at the same time prevent leakage of liquid into aerosol exit windows 30, particularly when the device is positioned above the horizontal. The outer diameter of the baffle 38 is maintained as large as possible to minimize formation of droplets in the upper regions of the liquid reservoir 14, and retaining accumulated large liquid particles below the baffle 38 resulting from the production of the aerosol. There is a critical dimension between the diffuser 24 and top surface of the liquid conduit 35. An additional purpose of the baffle 38 is to provide a stop mechanism for maintaining the critical distance between the diffuser 24 and the liquid orifice 21 of the liquid conduit, when the cap 20 has been fully threaded on housing 15.

Figure 9:
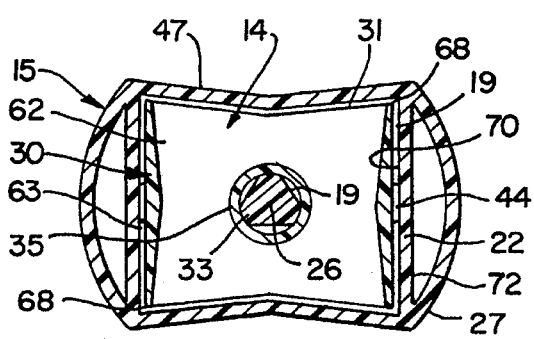
FIG. 9 sets forth a section view of the present invention taken along section lines 9—9 in FIG. 2.
Figure 10:
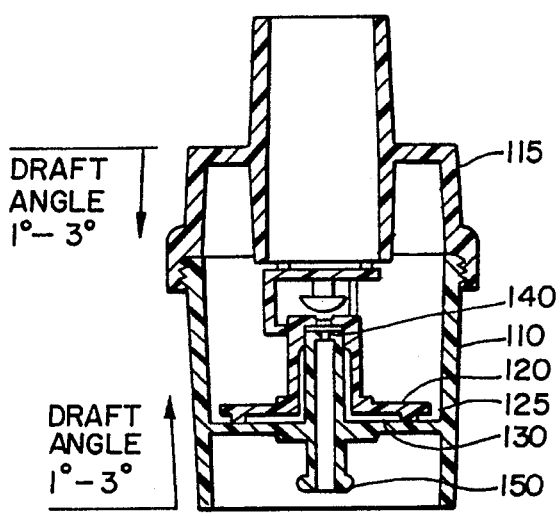
FIG. 10 sets forth a section view of a nebulizer of prior art, U.S. Pat. No. 4,566,452, in the vertical orientation, showing required draft angles.

On the external surface 63 of the internal component 30, is an external boss 44 and to separate and provide a narrow space 19 between the faces of the external surface 63 of the internal component 30 and the internal surface 70 of the "U" shaped liquid reservoir 14. The spacer 44 is discontinuous at 65 and terminates at the boundary of the internal diameter of the liquid conduit 35. Therefore, when the internal component 30 is interposed in the liquid reservoir, a narrow space 19 is defined, and is continuous from either side of the spacer 44, from the top of the internal component 30 to the external aspect of the triangular gas conduit 33, also revealed in FIG. 9, and continuous between the gas conduit 33 and liquid conduit 35, and terminates at the region between the gas nozzle 26 and the liquid orifice 21. Moreover, rather than having the spacer 44 projecting from the internal "U" component 30, the spacer 44 can also be employed within the liquid reservoir with the analogous relative position, and same function to maintain a constant narrow space 19.

The gas nozzle 26 and liquid orifice 21 are aligned. When the connector 17 is coupled to a pressurized gas source (25–50 psi), a high velocity gas stream exits the gas nozzle 26, and simultaneously through the liquid orifice 21. Thus a sub atmospheric pressure is created lateral to the high velocity gas stream in the region also defined as the narrow space 19, between the gas nozzle 26 and liquid orifice 21. Small particles of liquid exit the liquid orifice 21. These liquid particles further impinge on the diffuser 24 in which the liquid particles are finely divided to produce aerosol particles within the therapeutic range.

Again, referring to FIG. 7, the inside surface 62 of the internal component 30 is angled inward, and a small gap 31 exists along the peripheral edges of 68 and between the internal adjacent divergent walls 47. If in the event nebulizer 10 is lo positioned in the horizontal orientation with the divergent planar walls 22 facing downward, the liquid will gravitate to the corner region at the junction of the internal adjacent divergent walls 47, and divergent planar walls 22. To recapitulate, because of the inward angle of the internal adjacent divergent walls 47, and the inward angle of the internal surface 62 of the internal component 30, even small quantities of liquid will always gravitate along the peripheral edge 68 of the internal component 30, to the small gap 31 within the liquid reservoir 14. In this manner, liquid will be aspirated and directed to the liquid orifice 21 via the narrow space 19 as a result of the sub atmospheric pressure created by the high velocity gas stream exiting the gas nozzle 26, when nebulizer 10 is positioned from the vertical to above the horizontal.

Figure 8:
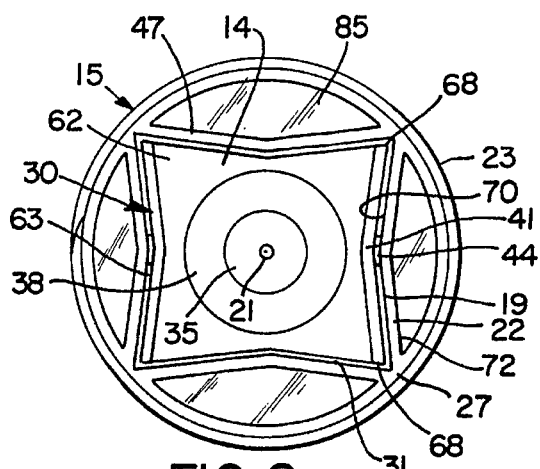
FIG. 8 sets forth a top view of the housing of an alternate embodiment of the present invention taken along section lines 7—7 in FIG. 2.

FIG. 8 sets forth a top view of an alternate embodiment taken along section lines 7—7 of nebulizer 10; and where like parts have like function and like reference numbers. In this embodiment the difference is the external surface 72 and internal surface 70 of divergent planar walls 22, and are angled inward to follow the same contour, of both the internal surface 62 and external surface 63 of the internal component 30 are angled inward. The spacer 44 as previously described above is also angled to follow the same contour and to maintain the small space 19. Likewise, the small gap 31 exists between the peripheral edge 68 of the internal component 30 and the internal adjacent divergent walls 47.

Figure 5:
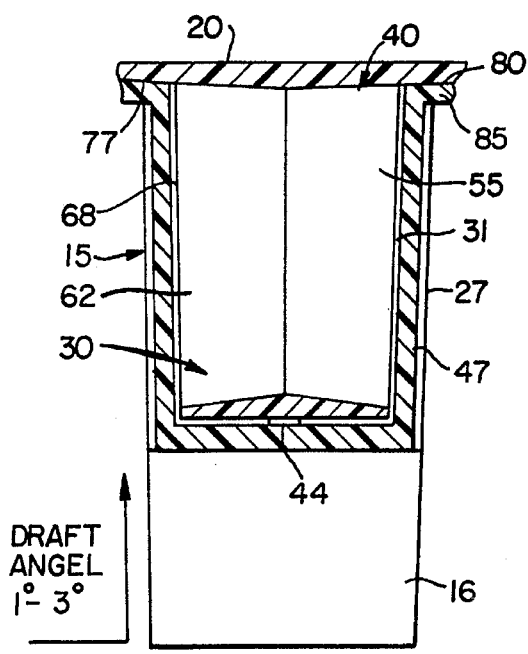
FIG. 5 sets forth a section view of the present invention taken along section lines 5—5 in FIG. 2

Referring now to FIG. 5. To simplify the drawing it is understood that the external thread 23 on housing 15, and internal thread 29 in the cap 20 has been omitted. When the cap 20 is threaded to housing 15 and given a sufficient torque, the inferior surface of 77 of cap 20 having the same conical shape as the superior surface 80 of the top wall 85, will provide a seal to prevent leakage of liquid medication. Moreover, when the cap 20 which is comprised of a flexible material such as polypropylene, is given a sufficient torque, a seal is provided at the top surface 41 of the internal component 30, and inferior surface 77 of the cap 20. This seal is designated by 40. The purpose of the seal will prevent additional ambient air to be aspirated from the narrow space 19 at the top surface 41 of the internal component 30, during the operation of nebulizer 10. As a result, this enhances the quantity of liquid to be aspirated for the generation of an aerosol from the vertical to above the horizontal, thereby increasing the aerosol output, and improving the overall performance of nebulizer 10.

During the operation of the present invention typically a T-adaptor with mouthpiece (not shown) is attached to an outlet 32 on cap 20. The aerosol is produced as previously explained, the aerosol particles with the carrier gas, drifts out of the shape reservoir 14 via the aerosol exit windows 28 and conduit 60, to the T-adaptor and mouthpiece. The patient inhales the aerosolized medication to the lungs and exhales through the T-adaptor and mouthpiece, creating the main gas flow where the aerosol particles and carrier gas is added.

Figure 11:
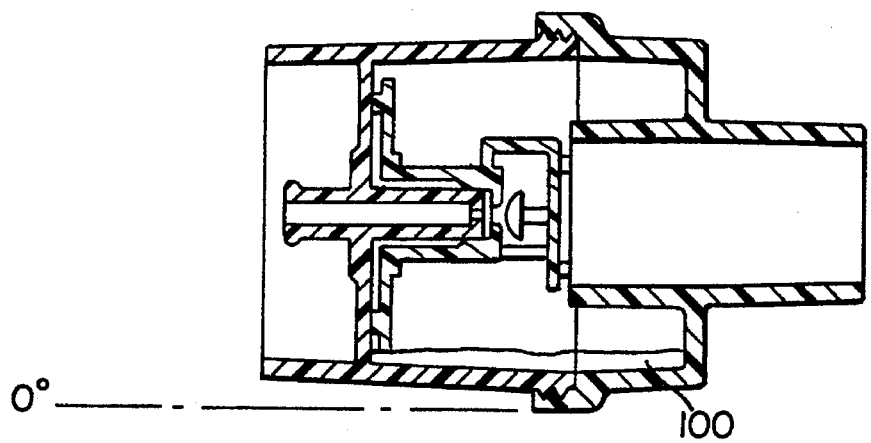
FIG. 11 sets forth a section view of a nebulizer of prior art, U.S. Pat. No. 4,566,452, showing liquid level in the horizontal orientation.

FIG. 11 is a sectional view of the prior art in the horizontal position. Also depicted is the liquid level 100. In the usual manner, the nebulizer is connected to a pressurized gas source via the air inlet 140, driving a high velocity jet of gas exiting the air nozzle 140. In the horizontal position, the liquid level 100 is sufficient to be aspirated through the space 125 and capillary passageway 130. It should be noted that ambient air is simultaneously being aspirated around the bottom flange 120 and space 125 above the liquid level 100. As the aerosol is being produced the liquid level 100 gradually decreases consequently the amount of ambient air aspirated becomes gradually greater than the amount of the liquid aspirated. This results in a gradual reduction in the quantity of aerosol output. Further decreases in the liquid level 100, and due to the typical draft angle of +1 to +3 degrees gradually moves the remaining quantity of liquid away from the space 125, until nebulization finally ceases, with a residual volume of liquid remaining in the reservoir 110. During the initial phase of operating the nebulizer, with a large enough liquid level 100, the aerosol output is sufficient, and draft angle has little effect in the horizontal position. However, the draft angle indeed has an effect with the smaller remaining volumes of liquid. Liquid must be available to the region of space 125 necessary for aspiration of the liquid, and therefore the production of aerosol. Although manufacturer's tout that this sidestream nebulizer will operate in the horizontal position, for the above stated reason, in actual practice, the prior art sidestream nebulizer's are almost never utilized in a horizontal position even though there are clinical applications.

Figure 12:
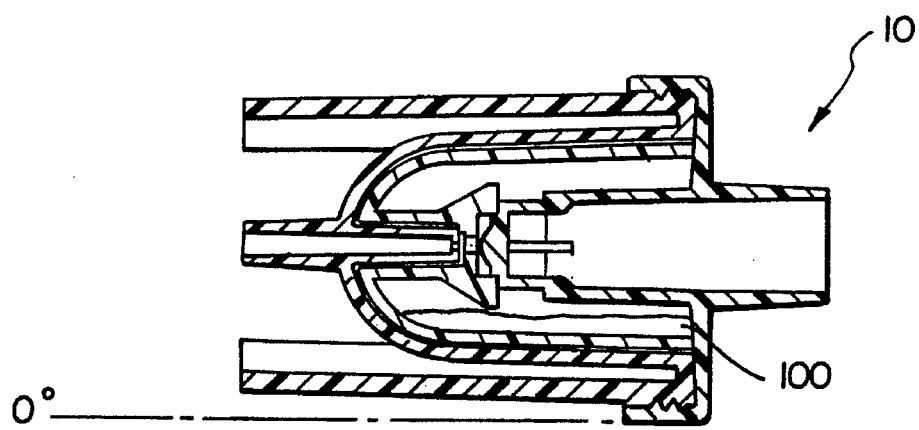
FIG. 12 sets forth a section view of the present invention taken along section lines 3—3 in FIG. 1, showing liquid level in the horizontal orientation.

FIG. 12 is the same sectional view of FIG. 3 of nebulizer 10 in the horizontal position showing the liquid level 100. The draft angles of +1 to +3 degrees to construct the housing 15, are consistent with injection molding methods In this example, and taken in conjunction with FIG. 7, either one of the two divergent planar walls 22 can be facing downward. In the horizontal orientation as shown, the internal surface 62 of the internal component 30, is angled for the liquid 100 to be directed or to gravitate to the small gap 31 along the full length and both sides of the peripheral edge 68 to be aspirated. Again, referring to FIG. 7, if the housing 15 is rotated by 90 degrees, with either adjacent divergent wall 47 facing downward in the horizontal position, liquid 100 will be directed in the same manner, to the same peripheral edge 68 on either side to the small gap 31. From the observation of FIG. 7, as housing 15 is completely rotated 360 degrees, the liquid 100 will always gravitate to the peripheral edge 68 of the internal component 30, to be aspirated, even with small quantities of liquid 100 to continue to aerosolize.

Figure 13:
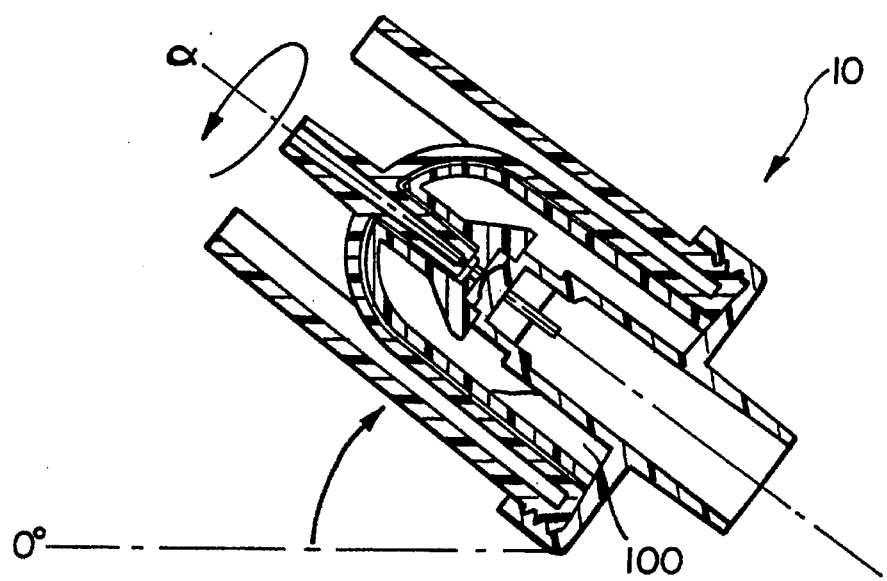
FIG. 13 sets forth a section view of the nebulizer of the present invention taken along section lines 3—3 in FIG. 1, showing liquid level in an orientation above the horizontal.

FIG. 13 is the same sectional view of FIG. 3 of nebulizer 10 in a position above the horizontal, showing liquid level 100. In this example, and again taken in conjunction with FIG. 7, either one of the two divergent planar walls 22 can be facing downward, at an angle above the horizontal. As previously stated, the internal surface 62 of the internal component 30 would be angled to cause the liquid 100 to gravitate to the peripheral edge of 68. The cap 20 with its inferior surface is conical in shape and with sufficient torque to the housing 15, a seal is provided (referred as 40 in FIG. 5) at the top surface 41 of the internal component 30. Therefore the efficiency of the aspiration is enhanced, particularly with decreased, small volumes of liquid 100. The liquid 100 is nebulizer 10 is rotated 360 degrees about the imaginary line alpha, the liquid 100 even in small quantities, will always be conveyed to the small gap 31.

Thus what has been revealed is a sidestream aerosol generator comprised of three parts, which are low cost, and to easy to manufacture components. The liquid medication is conveyed to a liquid orifice by a gas nozzle via an internal shape component which is inserted within the liquid reservoir of the nebulizer. A novel feature of the threaded cap provides a seal to prevent the additional aspiration of ambient air and therefore enhances aspiration of the liquid medication and will more efficiently generate an aerosol in all reference planes from the vertical to above the horizontal orientation.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the scope of the invention.

I claim:

1. An apparatus for aspirating and aerosolizing a liquid in a flow of gas under pressure comprising: a housing defining a liquid reservoir with walls of a predefined three dimensional geometric shape, an aerosol outlet located at a first axial end of said reservoir and a gas nozzle formed at a second axial end of said reservoir, said nozzle having means for connecting to a pressurized gas source;

an internal component having an operative position and being formed of a substantially flat member having an axial dimension and shaped along same to conform substantially with said reservoir along a bisecting cross section thereof, said internal component having a cylindrical liquid conduit with a first axial end connected to said internal component and a second axial end distal therefrom, said liquid conduit surrounding said gas nozzle when in said operative position;

wherein said internal component and said cylindrical liquid conduit form a minimal capillary space between, respectfully, said walls of said liquid reservoir and said gas nozzle, said cylindrical liquid conduit having a liquid orifice at said second axial end, wherein said gas nozzle and said liquid orifice are in fluid communication with said minimal capillary space.

2. The apparatus of claim 1 wherein the liquid reservoir has an open end and a closed end, and wherein the walls of said liquid reservoir define a substantially U-shaped configuration in at least one spatial dimension.

3. The apparatus of claim 1 wherein the liquid reservoir has an open end and a closed end, and wherein a portion of the walls of said liquid reservoir proximate said open end have a cross section defined by a plane parallel to the plane of the open end, said cross section comprising an internal and an external surface, said internal and external surfaces each comprising a vertex defined by a substantially equal inward angle.

4. The apparatus of claim 1 wherein the internal component further comprises a spacer means for maintaining said minimal capillary space between the internal component and the liquid reservoir.

5. The apparatus of claim 1 further comprising a thin annular disk supported proximate to the second axial end of said cylindrical liquid conduit.

6. The apparatus of claim 1 wherein said means for connecting to a pressurized gas source further comprises a triangular gas conduit.

7. The apparatus of claim 1 wherein the liquid reservoir has an open end and a closed end, and the walls of said liquid reservoir define a substantially V-shaped configuration in at least one spatial dimension.

8. The apparatus of claim 7 wherein the V-shaped configuration is further modified by parallel portions extending from the ends of each leg of the V-shape opposite the vertex and extending away from the vertex.

9. The apparatus of claim 1 wherein the housing comprises a cylindrical shell having an upper and a lower end.

10. The apparatus of claim 9 wherein said housing further comprises at least one window in a lateral surface thereof.

11. The apparatus of claim 9 wherein said cylindrical shell comprises an upper end wall substantially perpendicular to the wall of said shell at said upper end, said upper end wall being slightly conically angled.

12. The apparatus of claim 11 further comprising a threaded end cap, wherein said upper end wall is matingly threaded to receive said threaded end cap.

13. The apparatus of claim 12 wherein said cap further comprises a seal means for sealing the reservoir, the minimal capillary space and the internal component from the ambient.

14. The apparatus of claim 12 further comprising a thin annular disk supported proximate to the second axial end of said cylindrical liquid conduit, said washer having an internal diameter.

15. The apparatus of claim 14, wherein said threaded end cap further comprises a central hollow cylinder having a lateral wall, a first axial end in communication with the open end of said liquid reservoir, and a second axial end having an end wall, at least one opening through said lateral wall proximal to said end wall of said second axial end, a hemispherical projection having an outer diameter approximately equal to said internal diameter of said washer to define a diffuser, and a rotating baffle fitting within the internal diameter of the washer.

* * * * *